United States Patent [19]

Etheridge

[11] 4,043,202
[45] Aug. 23, 1977

[54] SAMPLE INJECTION SYSTEM FOR ANALYZERS

[75] Inventor: Jay D. Etheridge, Sand Springs, Okla.

[73] Assignee: Sun Oil Company of Pennsylvania, Philadelphia, Pa.

[21] Appl. No.: 668,780

[22] Filed: Mar. 19, 1976

[51] Int. Cl.² .............................................. G01N 1/22
[52] U.S. Cl. .............................................. 73/422 GC
[58] Field of Search ................................... 73/422 GC

[56] References Cited

U.S. PATENT DOCUMENTS

| 2,964,938 | 12/1960 | Fuller | 73/422 GC |
| 3,501,961 | 3/1970 | Hahle | 73/422 GC |
| 3,915,013 | 10/1975 | Gaeke | 73/422 GC |

Primary Examiner—S. Clement Swisher
Attorney, Agent, or Firm—J. Edward Hess; Donald R. Johnson

[57] ABSTRACT

A vacuum loop sample injection system, for use with gas chromatographs and other similar analyzer devices, in which the sample volume is collected within an enclosure having a known pressure, temperature, and volume so that the molecular quantity of a sample is used for each chromatograph test. The sample injection system operates by creating a vacuum within this enclosure and using this vacuum to slowly draw the sample in through a restriction until the predetermined pressure is obtained. The enclosure can be evacuated again by the vacuum source and refilled with the sample as many times as desired to wash any impurities out of the enclosure. Then the enclosure is placed in stream with the carrier gas for injection of the sample into the sample analyzer.

6 Claims, 4 Drawing Figures

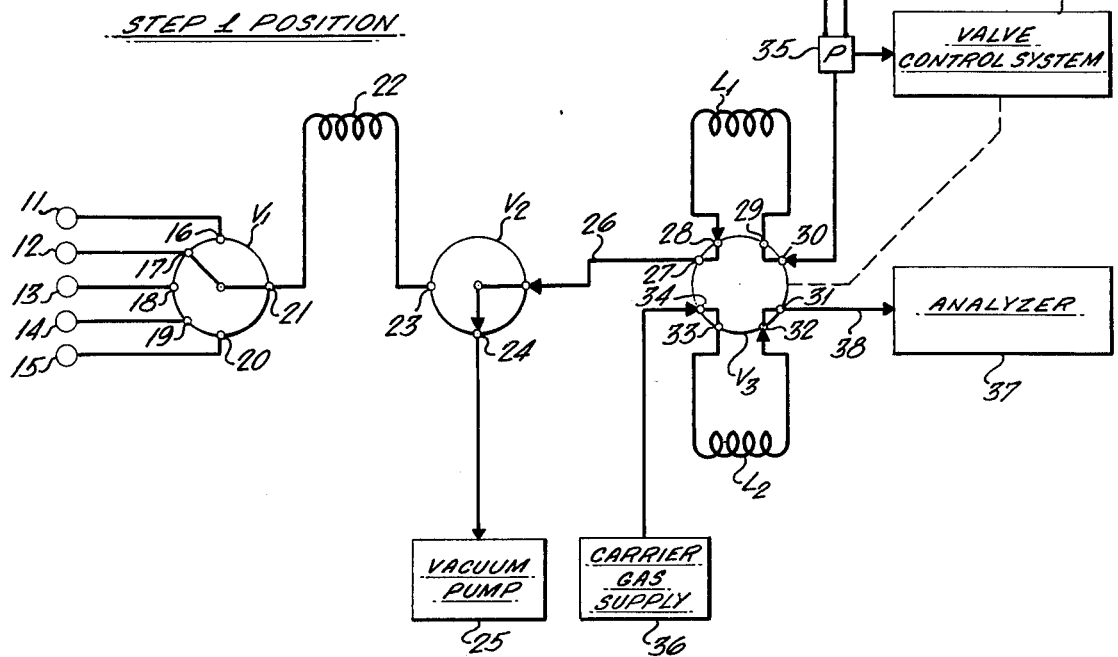
Fig. 1. STEP 1 POSITION
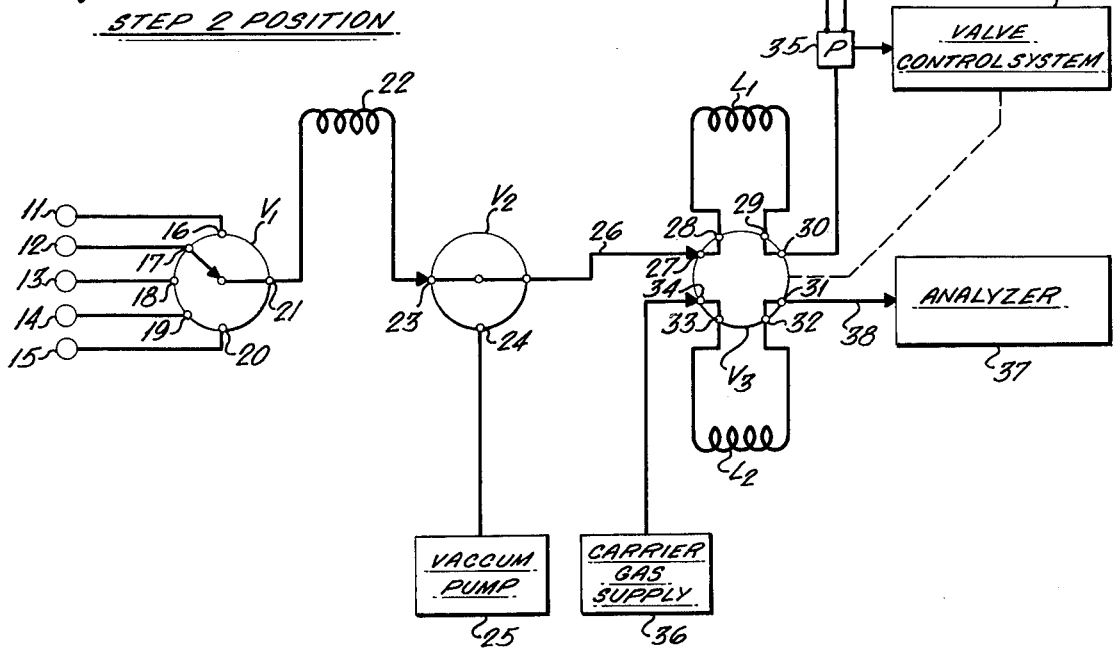
Fig. 2. STEP 2 POSITION

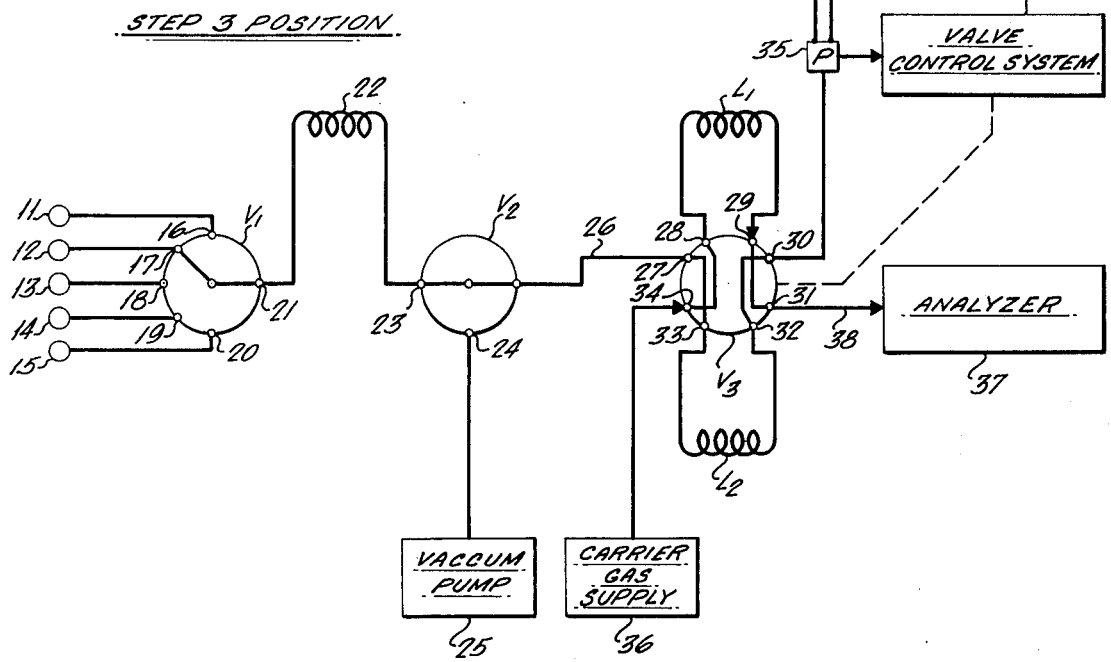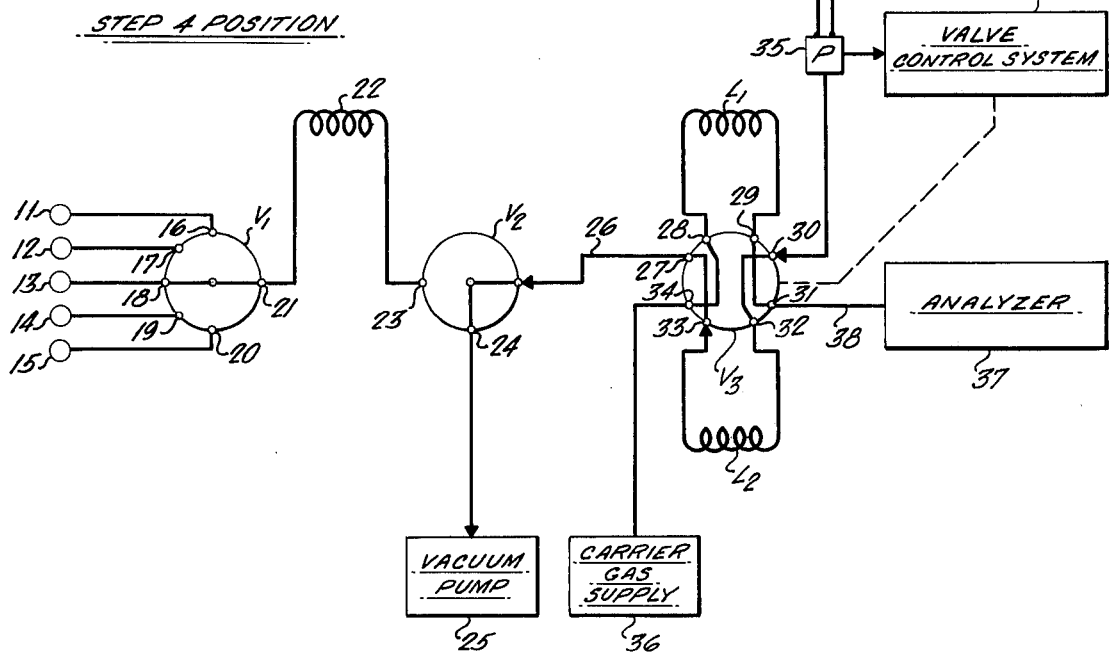

SAMPLE INJECTION SYSTEM FOR ANALYZERS

BACKGROUND OF THE INVENTION

This invention is related to sample injection systems for gas chromatographs and other similar analyzer devices, and more specifically to a sample injection system using a source of vacuum to obtain the sample.

There are several desirable requirements which should be met for a sample injection system. To achieve reliable, reproducible results, the sampling system should be able to inject a reproducible molecular quantity of sample each time. The injection system should also be designed to permit impurities to be washed out of the system before a sample is injected, so that the possibility of contamination of the sample from a previous sample is minimized. Preferably, the sampling system should be versatile enough so that it can receive samples contained at less than atmospheric pressure, as well as above. Another requirement for a sampling system is that it should be designed for efficient use of the sample by minimizing the amount of sample wasted and the amount of sample required for washing out the sampling system. In some instances, it is desirable that the sample injection system be designed so that it can be automated, so that continuous testing can be conducted as well as for obtaining better reproducability of results.

One of the problems today is that many of the sample injection systems available in the prior art fail to achieve all of the above noted requirements. One system in the prior art is a gas sampling valve in which the volume is trapped in a passage in the valve and quickly introduced into the carrier gas flow. In this system, temperature and volume can be accurately determined, but since the pressure is related to the flow rate, it often cannot be determined as accurately as is required. This system also fails to meet the requirements of sampling efficiency and the problems of being able to work with samples at less than atmospheric pressure.

Another method of obtaining a sample volume and injecting it in an anaylzer is to use the gas type syringe. This sampling system has problems meeting the requirements for reproductability of the sample size, because of the small volumes needed for analyzers, as well as the desirability that the system be easily adaptable to sample automation.

SUMMARY OF THE INVENTION

In accordance with a preferred embodiment a vacuum loop sample injection system for a chromatograph or other similar analyzer instrument in provided. Included in the sampling system is an enclosure having a known volume which is connected to a valve which can be switched in a sequence so that this enclosure is first evacuated by a vacuum pump, then connected to a source of sample fluid so that the pressure difference between the enclosure and the source container causes the sample to slowly flow through a restrictor and into the enclosure, and finally connected to a carrier gas supply when the pressure within the enclosure has reached a predetermined amount, wherein the sample trapped within the enclosure is carried by the carrier gas into the gas chromatograph system or other analyzer. For purposes of rinsing the enclosure to clean out contaminants, instead of immediately connecting the enclosure to the carrier gas, it can again be connected to the vacuum pump and then to the same sample source as many times as is deemed necessary before connection to the carrier gas for injection into the analyzer instrument. A pressure sensor system connected to the enclosure indicates when the predetermined pressure has been reached. Included also in this sample injection system is a system for selecting the sample source which is to be connected to the enclosure for injection into the chromatograph.

This sample injection system meets all of the above requirements noted for a gas sampling system for a chromatograph. Since the entire system can be mounted in an oven and maintained at a constant temperature, the volume of the enclosure is constant, and the same pressure is obtained each time a sample is isolated within the enclosure, and the same molecular quantity of sample will be injected into the gas chromatograph or other analyzer each time. Using the vacuum pump system and rinsing out the sample loop at least one or two times before it is placed in line with the carrier gas for injection into the gas chromatograph, usually is sufficient to minimize the possibility of contamination from the previous sample injected by the system.

Another advantage derived from using a vacuum pump is that it permits the system to work with samples which are maintained at less than atmospheric pressure, as well as those at greater than atmospheric pressure. With proper selection of the size of the enclosure and the conduit used to connect the various elements of the system, the sampling efficiency can be maintained at a high level so that the amount of sample wasted is minimized. The system is designed so that its control is determined solely by the position of the valves. This feature enables the system to be easily adapted to an automatic control system so that an entire series of samples can be individually injected into the chromatograph and analyzed in a sequential fashion.

A better understanding of the invention and its advantages can be seen in the following description of the figures and preferred embodiment.

DETAILED DESCRIPTION OF THE DRAWINGS AND PREFERRED EMBODIMENT

FIG. 1 illustrates a schematic drawing of the vacuum loop sample injection system with the valves in position for Step 1.

FIGS. 2-4 are the same as FIG. 1 with the valves shown in their positions for Steps 2, 3 and 4, respectfully.

The vacuum loop gas injection system is designed so that it can be mounted within an oven such as the oven containing the chromatograph or other analyzer. However, the oven and controls for maintaining the proper temperature therein are not illustrated in the drawing, since they are not part of the invention and the illustration thereof is not necessary for one skilled in the art to practice this invention.

The injection system has three selector valves, V1, V2, and V3 which determine the manner in which the elements of the injection system are connected. These selector valves, with their respective actuator systems, can be any of the many conventional valves currently availabe for use with gas chromatographs and other similar analyzer systems, or a rotary valve similar to that shown in U.S. Pat. No. 3,223,123 issued to E. T. Young.

Valve V1 is connected so that it can receive samples from a selected number of containers. As is shown in FIG. 1, five sample containers 11, 12, 13, 14 and 15, are connected to ports 16, 17, 18, 19 and 20 on valve V1 through their respective conduit lines. While only five sample containers are shown connected to valve V1, it can be appreciated that the capacity of the injection system can be increased by selection of a valve with a greater capacity. Connected to port 21 of valve V1 is a restriction 22 which acts to slow the flow rate of the sample material entering the injection system as well as to smooth out the flow. Preferably, restrictor 22 can be made from a length of small diameter capillary tubes with an inside diameter small enough so that several seconds are necessary for the sample enclosure or loop in the injection system to be filled.

Valve V2 acts as a control valve and has two positions in which either port 23, which is connected to restrictor 22, or port 24, which connects to vacuum pump 25, is connected to port 27 of valve V3 conduit 26.

Valve V3 also is a two position valve and has eight ports which are interconnected in a manner which will be described below. Two sample loops, L1 and L2, serve as sample enclosures and are connected to valve V3 through ports 28 and 29, and 32 and 33, respectively. While one sample loop would be adequate, more efficient operation is permitted when two loops are used. It should be noted that other alternatives to using sample loops are possible, such as a small passageway within the valve V3. Pressure sensor system 35 is connected to port 30 and carrier gas supply 36 is connected to port 34. An analyzer of gas chromatograph 37, which receives the sample volume, is connected to port 31 of valve V3 through injection line 38.

Valve V3 has a first position, which is illustrated in FIGS. 1 and 2, wherein loop L1 is in series with conduit 26 and pressure sensor system 35, and loop L2 is in series with carrier gas supply 36 and injection line 38 leading to analyzer 37. The second position of valve V3 has loop L1 connected in series with carrier gas supply 36 and analyzer 37 and loop L2 connected in series with conduit 26 and pressure sensor 35.

Included within pressure sensor system 35 can be a system for producing a signal which indicates that the pressure sensor has determined that the pressure within a loop has reached a predetermined amount. This signal can be in the form of a light 39 or can be a signal sent to a valve control system for automatically changing the position of valve V3. A more detailed explanation of the operation of these systems wil be provided below.

When operating the vacuum loop sample injection system, a desired number of sample containers can be connected to the ports of valve V1. Valve V1 is then set to connect one of the valve ports associated with a particular sample to the exit port 21, such as port 17 which is illustrated in FIG. 1. Valve V2 is set so that vacuum pump 25 is connected to conduit 26. When valve V3 is in the position indicated in FIG. 1, loop L1 will be connected to vacuum pump 25 through valve V2 and also to pressure sensor system 35. At the same time loop L2 is connected in series with carrier gas supply 36 and analyzer 37. What is taking place at this time, is that any sample material that is in loop L2, is being injected into analyzer 37 by the flow of carrier gas from carrier gas supply 36. Also, at the same time, a vacuum is being created within loop L1. The injection system is now at its Step 1 position, as is shown in FIG. 1.

In the Step 2 position, the position of valve V2 is changed so that loop L1 is connected to a sample source, such as container 12, through valves V1 and V2 and restrictor 22. However, the position of valve V3 remains unchanged and carrier gas is still flowing through loop L2. In Step 2, a vacuum is present within loop L1 which acts to pull sample material from container 12 eventually into loop L1. Step 2 continues until the pressure within loop L1 rises to the predetermined amount set on pressure sensor system 35.

Because of restrictor 22, the time to reach this pressure will be several seconds. Once pressure sensor system 35 indicates that the predetermined pressure has been reached, valve V3 then changes into its second position as is illustrated in FIG. 3. The change of valve V3's position can be accomplished manually by having an operator switch the valve position when light 39 lights up or the valve position can be done automatically by having a signal sent to a valve control system 40 from pressure sensor system 35.

For purposes of rinsing the injection system out so that contamenants are removed before the sample is analyzed, Step 3 can be delayed so that Step 1 and Step 2 can again be repeated, as often as is deemed necessary. In this manner, the sample is drawn back out of loop by vacuum pump 25 and new amounts of sample drawn back into the loop. After repeating this sequence of Step 1 and Step 2 a few times, Step 3 can then be initiated.

With the injection system in the Step 3 position, loop L1 is now connected to carrier gas supply 36 and analyzer 37 so that the carrier gas forces the sample collected within loop L1 into analyzer 37 to be analyzed.

Also in the Step 3 position, loop L2 is in position to receive the next sample to be analyzed, in a similar manner as described above for loop L1. Vacuum pump 25 is connected to loop L2 through valve V2, as illustrated in FIG. 4 for the Step 4 position. Valve V1 is also switched to connect the next sample, sample 13 at port 18, to restrictor 22 for later connection to loop L12.

The rinse cycle for loop L2 can now begin by switching the positions of valve V2 so that loop L2 is filled and evacuated a few times as discussed above for loop L1. After an appropriate number of rinses, the position of valve V3 can be reversed back to the position shown in FIGS. 1 and 2 so that the sample collected in loop L2 is again injected into analyzer 37 and loop L1 can be rinsed and filled with the next sample, sample 14.

The pressure sensor system 35 can include a pressure transducer interconnected with a voltage divider circuit so that when the pressure in the loop reaches the predetermined level, the transducer and the voltage divider circuit reach a certain voltage or condition which causes light bulb 39 to light up. The valve control system can be any electrical system which would cause valve V3 to change positions once a certain voltage or condition was reduced by the pressure sensor system 35. Systems which perform these functions are readily available to those skilled in the art.

While this sample injection system is primarily designed for laboratory use, it can be equally applicable to process control. Instead of using valve V1, restrictor 22 may be directly connected to a stream in some process. Another alternative would be to circulate several streams through their own sample container in which a sample can be isolated at will and tested as illustrated above.

While a particular embodiment of this invention has been shown and described, it is obvious that changes and modifications can be made without departing from the true spirit and scope of the invention. It is the intention of the appended claims to cover all such changes and modifications.

The invention claimed is:

1. A vacuum loop sample injection system for injecting a predetermined amount of sample from a sample source into a system for analyzing said sample, and comprising:
   a. a vacuum source;
   b. means defining an enclosure having a predetermined volume;
   c. means for detecting the pressure within the enclosure means and for producing a signal indicating that pressure within said enclosure means has reached a predetermined amount;
   d. a source of carrier gas;
   e. means for selectively connecting the enclosure means to be vacuum source, so that the fluid inside the enclosure means is evacuated;
   f. means for selectively connecting the enclosure means to the sample source, so that the vacuum created within the enclosure means causes a portion of said sample to fill the enclosure;
   g. means for selectively placing the enclosure means in series with the carrier gas source and the sample analyzer system, so that the carrier gas forces the sample isolated in the enclosure into the analyzing system; and
   h. means for actuating the means for selectively placing the enclosure means in series with the carrier gas source and the sample analyzing means in response to the signal from the pressure detecting means indicating that the predetermined pressure in the enclosure means has been reached, so that when the enclosure means is being filled with the sample and reaches a predetermined pressure, the enclosure means is switched in series with the carrier gas source so that the predetermined amount of sample is injected in the sample analyzer.

2. The vacuum loop sample injection system recited in claim 1, further comprising means for restricting the flow of sample into the enclosure means, so that a slow, even flow of sample into the enclosure means is obtained.

3. the vacuum loop sample injection system recited in claim 1, wherein the sample source includes a plurality of sample containers and further comprises means for selectively connecting a chosen individual sample container to be connected to the enclosure means by the means for connecting the enclosure means to the sample source.

4. The vacuum loop sample injection system recited in claim 1, further comprising:
   a. second means defining an enclosure having a predetermined volume;
   b. means for placing said second enclosure means in series with the carrier gas source and the sample analyzer system when the first enclosure means is connected to the vacuum source; and
   c. means for connecting said second enclosure with the vacuum means or sample source when the first enclosure means is in series with the carrier gas source and the sample analyzer.

5. The vacuum loop sample injection system recited in claim 4, wherein the sample source includes a plurality of sample containers and further comprises means for selectively connecting a chosen individual sample container to be connected to the enclosure means by the means for connecting the enclosure means to the sample source.

6. The vacuum loop sample injection system recited in claim 5, further comprising means for restricting the flow of sample into the enclosure means, so that a slow, even flow of sample into the enclosure means is obtained.

* * * * *